United States Patent
Zeidan et al.

(10) Patent No.: US 10,932,686 B2
(45) Date of Patent: Mar. 2, 2021

(54) IDENTIFYING ACTIVATIONS IN AN ATRIAL FIBRILLATION ELECTROGRAM

(71) Applicant: Biosense Webster (Israel) Ltd., Yokneam (IL)

(72) Inventors: Ziyad Zeidan, Zemmer (IL); Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 76 days.

(21) Appl. No.: 15/986,238

(22) Filed: May 22, 2018

(65) Prior Publication Data
US 2019/0357791 A1    Nov. 28, 2019

(51) Int. Cl.
*A61B 5/046*   (2006.01)
*A61B 5/042*   (2006.01)
*A61B 5/0456*  (2006.01)

(52) U.S. Cl.
CPC .............. *A61B 5/046* (2013.01); *A61B 5/042* (2013.01); *A61B 5/0456* (2013.01)

(58) Field of Classification Search
CPC ..... A61B 5/046; A61B 5/0456; A61B 5/7235; A61B 5/0452; A61B 5/04012
USPC ........................................................ 600/518
See application file for complete search history.

(56) References Cited

U.S. PATENT DOCUMENTS

| | | | |
|---|---|---|---|
| 8,386,024 B2 | 2/2013 | Gunderson et al. | |
| 8,948,837 B2 | 2/2015 | Harlev et al. | |
| 9,002,442 B2 | 4/2015 | Harley et al. | |
| 9,020,584 B2 | 4/2015 | Moulder et al. | |
| 9,510,769 B2 | 12/2016 | Harlev et al. | |
| 9,642,550 B2 | 5/2017 | Ng | |
| 2010/0274150 A1 | 10/2010 | Harley et al. | |
| 2012/0184863 A1 | 7/2012 | Harlev et al. | |
| 2013/0281870 A1 | 10/2013 | El Haddad et al. | |
| 2015/0088019 A1 | 3/2015 | Macadam et al. | |
| 2015/0208938 A1 | 7/2015 | Houben et al. | |
| 2015/0208942 A1 | 7/2015 | Bar-Tal et al. | |
| 2015/0230721 A1 | 8/2015 | Lo et al. | |
| 2016/0331258 A1* | 11/2016 | Du | A61B 5/04012 |

OTHER PUBLICATIONS

European Search Report dated Aug. 7, 2019, Application No. EP 19 17 5577.

(Continued)

*Primary Examiner* — Amanda K Hulbert
*Assistant Examiner* — Philip C Edwards

(57) ABSTRACT

A system includes an electrical interface and a processor configured to receive, via the electrical interface, a signal sensed by at least one electrode in contact with tissue of a subject's heart, the signal spanning successive time periods that are each of length T1 and including multiple signal points, to calculate respective thresholds for the time periods, to select a set of points that includes, for each of the time periods, a signal point of greatest magnitude in the time period, provided that the greatest magnitude is greater than the threshold for the time period, to remove, from the set, one of any pair of the selected points that are within an interval T2 of one another, T2 being less than T1, and to generate, subsequently to the removing, an output that is based on the points remaining in the set corresponding to respective electrical activations of the tissue.

18 Claims, 3 Drawing Sheets

(56) References Cited

OTHER PUBLICATIONS

Jiapu Pan et al: "A Real-Time QRS Detection Algorithm", IEEE Transactions on Biomedical Engineering, vol. BME-32, No. 3, Mar. 31, 1985, pp. 230-236, XP055129317, ISSN: 0018-9294, DOI: 10.1109/TBME.1985.325532 * p. 233, line 28—line 36 * p. 231, col. 2, line 30—line 33 *.

* cited by examiner

IDENTIFYING ACTIVATIONS IN AN ATRIAL FIBRILLATION ELECTROGRAM

FIELD OF THE INVENTION

The present invention relates generally to the field of electrophysiology, and particularly to cardiac arrhythmias such as atrial fibrillation.

BACKGROUND

Atrial fibrillation is an abnormal heart rhythm characterized by rapid and irregular beating of the atria. Typically, the shape of an atrial fibrillation cardiogram varies over different anatomical sites, and/or over the duration of the recording. Consequently, conventional methods of annotating an electrogram signal to determine a Local-Activation-Time (LAT) are not appropriate for this type of arrhythmia.

US Patent Application Publication 2015/0208942, whose disclosure is incorporated herein by reference, describes a catheterization of the heart that is carried out by inserting a probe having electrodes into a heart of a living subject, recording a bipolar electrogram and a unipolar electrogram from one of the electrodes at a location in the heart, and defining a window of interest wherein a rate of change in a potential of the bipolar electrogram exceeds a predetermined value. An annotation is established in the unipolar electrogram, wherein the annotation denotes a maximum rate of change in a potential of the unipolar electrogram within the window of interest. A quality value is assigned to the annotation, and a 3-dimensional map is generated of a portion of the heart that includes the annotation and the quality value thereof.

SUMMARY OF THE INVENTION

We have developed technological solutions for specific real-world technical problems related to atrial fibrillation, such as the problems described above in the Background. Our technological solutions (which cannot be performed by humans) provide consistent annotation results, e.g., in real-time, for a physician performing an electrophysiological (EP) procedure, when applied, for example, to bipolar signals read from a mapping catheter (which may be disposed, for example, inside a living heart) during atrial fibrillation. Technical features of the invention were devised, in the form of embodiments described herein, to improve the functioning of EP systems, and thereby improve the health of subjects who undergo EP procedures.

We note that our technological solutions cannot be implemented directly on a generic computer because our solutions require the implementation of various components designed specifically for EP procedures, such as, for example, an EP catheter to map the electrogram signals, and sensors on the EP catheter that allow the system to ascertain the sites on the live beating heart from which the electrogram signals originated. For example, our technological solutions, as described and illustrated herein, solve the problem of mapping and measuring atrial fibrillation (a real-life phenomenon) and annotating the intracardiac signals that originate therefrom. Thus, our technological solutions advance the EP art in arriving at the inventive concept and technical features necessary to map and annotate the intracardiac signals originating from atrial fibrillation.

Accordingly, there is provided, in accordance with some embodiments of the present invention, a system that includes an electrical interface and a processor. The processor is configured to receive, via the electrical interface, a signal sensed by at least one electrode in contact with tissue of a heart of a subject, the signal spanning successive time periods that are each of length T1 and including multiple signal points. The processor is further configured to calculate respective thresholds for the time periods, and to select a set of points that includes, for each of the time periods, a signal point of greatest magnitude in the time period, provided that the greatest magnitude is greater than the threshold for the time period. The processor is further configured to remove, from the set, one of any pair of the selected points that are within an interval T2 of one another, T2 being less than T1, and to generator, subsequently to the removing, an output that is based on the points remaining in the set corresponding to respective electrical activations of the tissue.

In some embodiments, the processor is configured to receive the signal while the heart of the subject experiences atrial fibrillation.

In some embodiments, T1 is between approximately 80 and approximately 120 ms.

In some embodiments, T2 is between approximately 80 and approximately 120 ms.

In some embodiments,
the interval is a first interval,
the time periods include a first time period, a second time period that immediately follows the first time period, and a third time period that immediately follows the second time period, the set of points includes a first-period signal point in the first time period and a second-period signal point in the second time period,
the processor is further configured to:
identify a first global extremum of the signal within a second interval T3 from the first-period signal point, and
identify a second global extremum of the signal within the second interval from the second-period signal point, and
the processor is configured to calculate the threshold for the third time period as a product of (a) a coefficient that is less than one, and (b) a minimum of (i) a first-global-extremum magnitude of the first global extremum and (ii) a second-global-extremum magnitude of the second global extremum.

In some embodiments, the coefficient is between approximately 0.1 and approximately 0.5.

In some embodiments, T3 is from about 250 to about 350 ms.

In some embodiments, the processor is configured to remove, from any pair of the selected points that are within T2 of one another and are respectively not within T2 of any other one of the selected points, one of the pair having a smaller magnitude than that of the other one of the pair.

In some embodiments, the processor is configured to generate the output by annotating the signal to indicate that the points remaining in the set correspond to the respective electrical activations.

In some embodiments, the processor is configured to generate the output by:
calculating a length of a cycle of electrical activation from the points remaining in the set, by calculating at least one time interval between two of the points remaining in the set, and
displaying the length of the cycle.

There is further provided, in accordance with some embodiments of the present invention, a method that includes receiving a signal provided by at least one electrode in contact with tissue of a heart of a subject, the signal spanning successive time periods that are each of length T1 and including multiple signal points. The method further includes calculating respective thresholds for the time periods, and selecting a set of points that includes, for each of the time periods, a signal point of greatest magnitude in the time period, provided that the greatest magnitude is greater than the threshold for the time period. The method further includes removing, from the set, one of any pair of the selected points that are within an interval T2 of one another, T2 being less than T1, and generating an output that is based on the points remaining in the set corresponding to respective electrical activations of the tissue.

It is noted that the technical features described herein cannot be provided by skilled humans experienced in the interpretation of intracardiac signals, at least because of the inherent difficulty in interpreting atrial fibrillation signals, and/or by virtue of the fact that the solutions described herein may be provided in virtually real-time. For example, a signal may be annotated within 10 seconds, five seconds, or one second of receipt of the signal.

The present invention will be more fully understood from the following detailed description of embodiments thereof, taken together with the drawings, in which:

DETAILED DESCRIPTION OF EMBODIMENTS

Overview

Figure 1:
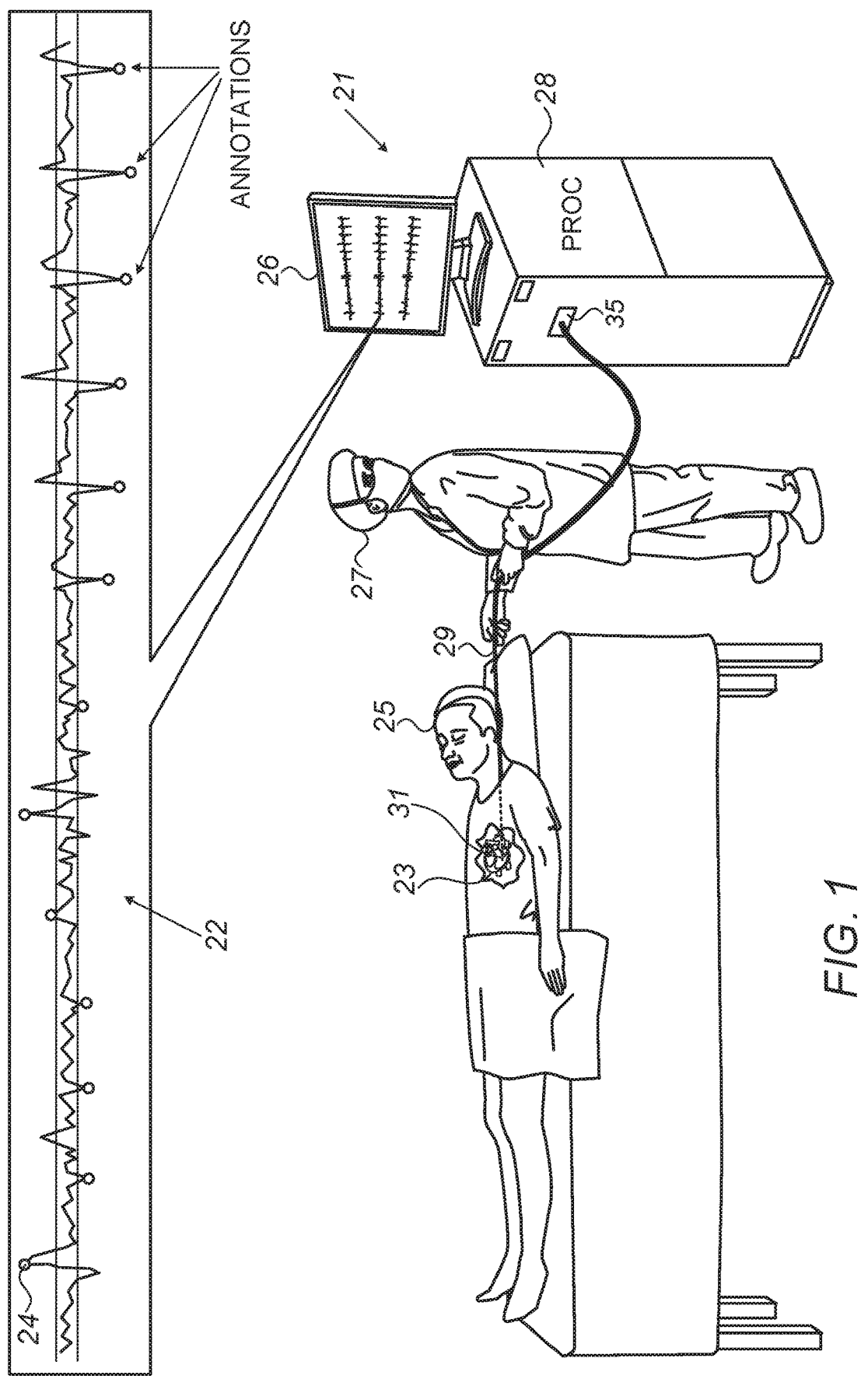
FIG. 1 is a schematic illustration of a system for annotating an electrogram signal, in accordance with some embodiments of the present invention.

In some cases, a physician may wish to understand the manner in which the wavefront of electrical activation propagates through the cardiac tissue of a subject during each cardiac cycle. In such cases, a plurality of electrodes may be used to sense or record electrogram signals at different respective sites on the cardiac tissue. For each of the signals, the physician may attempt to identify any electrical activation points, i.e., any points in the signal that correspond to an instance at which the wavefront passed through the site at which the signal was acquired. Unfortunately, however, in cases of atrial fibrillation or other arrhythmias, it may be difficult, even for an experienced EP physician, to identify any activation points, due to the irregularity and/or variability of the electrogram signals. For example, whereas regular electrograms include regularly-spaced, sharp peaks that clearly indicate activations, irregular electrograms may exhibit a wide variety of different forms, and may include numerous small peaks in close succession, with none of the peaks clearly indicating an activation.

To address this challenge, embodiments of the present invention provide techniques for automatically identifying activation points even in electrograms that exhibit atrial fibrillation or other arrhythmic behavior. Per these techniques, a processor divides the signal into successive time periods that are each of a predefined length T1, T1 typically being slightly greater than the minimum expected cycle length (i.e., the minimum expected length of the cycle of electrical activation). In each of the time periods, the processor identifies the positive or negative peak whose magnitude is greater than that of any other point in the time period and is also greater than a dynamically-calculated threshold (provided that such a peak exists). These peaks are referred to herein as "candidate activation points," in that each peak may correspond to an activation.

Next, the processor iterates over the identified candidate activation points. For any pair of these points that are within an interval T2 of one another, T2 typically being around the minimum expected cycle length, the processor discards one of the two points. The remaining candidates are then assumed to be activation points corresponding to different respective activations.

Finally, the processor annotates the signal to indicate that the remaining candidate points correspond to different respective activations, and/or displays other output that is based on these points corresponding to different respective activations. For example, the processor may calculate a cycle length from the respective times of the points and then display the cycle length, e.g., by including the cycle length in an electroanatomical map. Alternatively or additionally, by processing multiple signals acquired from different respective areas of tissue, the processor may compute the activation sequence for the tissue, i.e., the sequence in which the areas are activated during each cardiac cycle.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

System Description

Reference is initially made to FIG. 1, which is a schematic illustration of a system 21 for annotating an electrogram signal 22, in accordance with some embodiments of the present invention.

FIG. 1 shows an EP physician 27 operating an EP catheter 29, a distal end 31 of which is disposed within the heart 23 of a subject 25. As physician 27 moves distal end 31 of catheter 29 along the inner or epicardial surface of the heart, one or more electrodes at the distal end of the catheter, which are in contact with tissue of the heart, sense electrogram signals 22 generated by the tissue. Such signals may be sensed, for example, while heart 23 experiences atrial fibrillation or any other arrhythmia, such as atrial flutter or atrial tachycardia. (In some cases, the arrhythmia may be induced by the physician prior to the procedure.)

A processor (PROC) 28 receives signals 22 via an electrical interface 35, such as a socket or port, and processes these signals as described below with reference to FIG. 2. In response to processing the signals, processor 28 generates an output, which typically includes a visual output displayed on a display 26. For example, processor 28 may annotate at least one signal 22 to show the activation points of the signal, and then display the annotated signal on display 26.

In annotating the signal, processor 28 may, for example, place a marker 24 over each activation point.

In general, the electrodes at distal end 31 may be arranged in any suitable configuration, such as a circular, linear, or multi-spline configuration. Typically, each signal 22 is a bipolar signal, in that the signal represents the voltage between a respective pair of the electrodes at distal end 31. Alternatively, however, at least one signal may be a unipolar signal, in that the signal represents the voltage between one of the electrodes and a reference electrode that is coupled externally to the subject.

In general, processor 28 may be embodied as a single processor, or as a cooperatively networked or clustered set of processors. In some embodiments, the functionality of processor 28, as described herein, is implemented solely in hardware, e.g., using one or more Application-Specific Integrated Circuits (ASICs) or Field-Programmable Gate Arrays (FPGAs). In other embodiments, the functionality of processor 28 is implemented at least partly in software. For example, in some embodiments, processor 28 is embodied as a programmed digital computing device comprising at least a central processing unit (CPU) and random access memory (RAM). Program code, including software programs, and/or data are loaded into the RAM for execution and processing by the CPU. The program code and/or data may be downloaded to processor 28 in electronic form, over a network, for example. Alternatively or additionally, the program code and/or data may be provided and/or stored on non-transitory tangible media, such as magnetic, optical, or electronic memory. Such program code and/or data, when provided to processor 28, produce a machine or special-purpose computer, configured to perform the tasks described herein.

Figure 2:
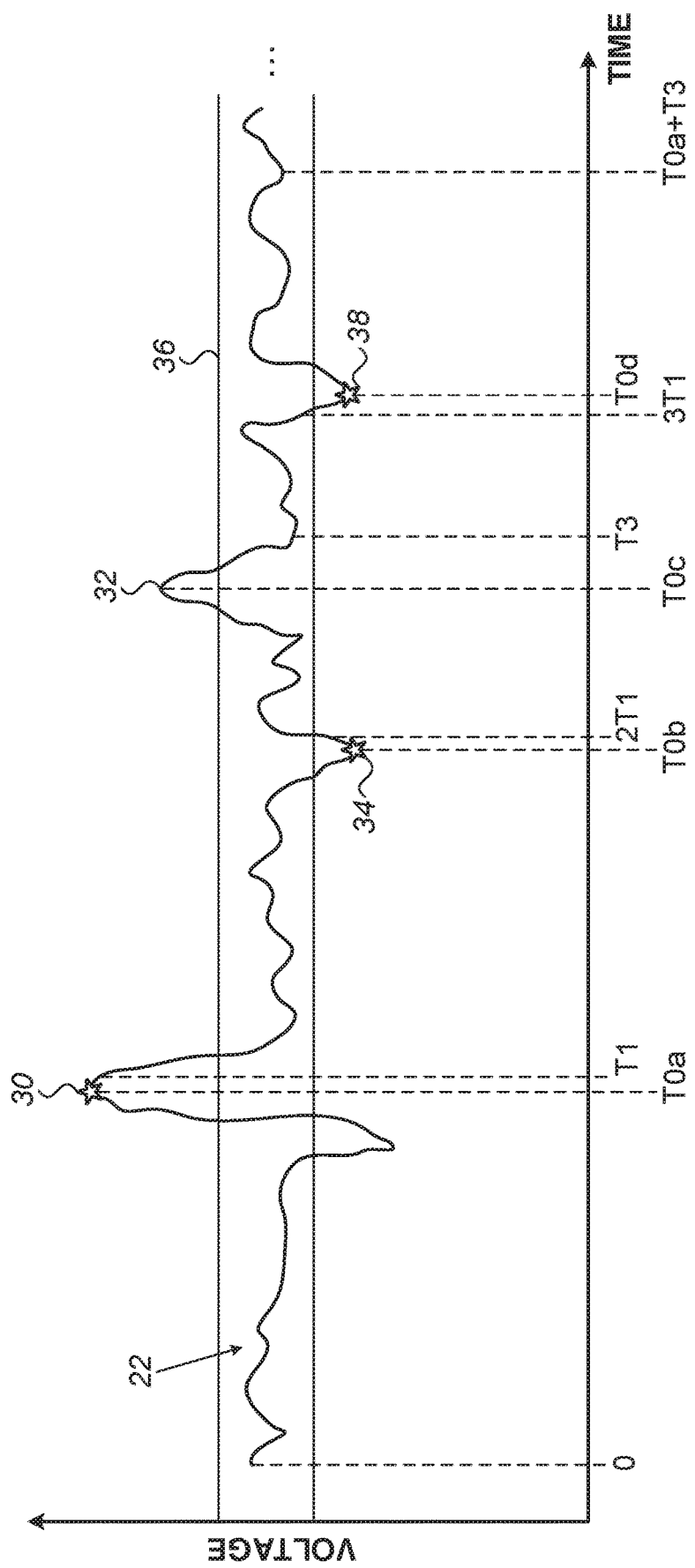
FIG. 2 is a schematic illustration of an identification of activation points in an electrogram signal, in accordance with some embodiments of the present invention.

Reference is now made to FIG. 2, which is a schematic illustration of an identification of activation points in an electrogram signal, in accordance with some embodiments of the present invention.

Typically, in processing each signal 22, processor 28 divides the total period that is spanned by the signal into successive smaller time periods, each being of length T1 (e.g., 100 ms). (Thus, the first time period spanned by the signal runs from 0 to time T1, the second time period runs from T1 to 2T1, etc.) Processor 28 further calculates respective thresholds for the time periods, as further described below. (Equivalently, it may be said that processor 28 calculates a single threshold, which is updated for each of the time periods.) Processor 28 further selects a set of candidate activation points that includes, for each of the time periods, the point (or "peak") of greatest magnitude in the time period, provided that the greatest magnitude is greater than the threshold for the time period and is also greater than a predefined noise threshold (e.g., 0.05 mV), indicated in FIG. 2 by noise-threshold lines 36. (Typically, the set of candidate activation points does not include any points other than the points of greatest magnitude.) Finally, as further described below, processor 28 removes, from the set of candidate activation points, one of any pair of the candidate points that are within an interval T2 of one another, T2 being less than T1 (e.g., 80 ms). The points remaining in the set are then assumed to be activation points.

Typically, processor 28 processes the time periods in sequence. For each of the time periods, processor 28 calculates the threshold based on a global extremum of the signal in or near the time period. For example, for any three consecutive time periods, following the selection of a respective candidate activation point from each of the first two time periods, the threshold T for the third time period may be calculated as T=C*min(GE1, GE2), where C is a coefficient that is less than one (e.g., approximately 0.3), GE1 is a global extremum of the signal within an interval T3 from the first candidate activation point, T3 being greater than T1 (e.g., approximately 250 ms), and GE2 is a global extremum of the signal within T3 from the second candidate activation point. Processor 28 then selects another candidate activation point from the third time period, provided that the magnitude of this point is greater than both the threshold T and the predefined noise threshold.

For example, in processing the example signal shown in FIG. 2:

(i) Processor 28 identifies the global extremum 30 of the signal within T3 from the start time of the signal (i.e., 0). In other words, processor 28 identifies the positive or negative peak (i.e., the maximum or minimum) of the signal within the interval 0-T3 that has the greatest magnitude, relative to all other peaks within this interval.

(ii) Processor 28 calculates a first threshold value by multiplying the magnitude of extremum 30 by coefficient C.

(iii) Processor 28 identifies the point of greatest magnitude in the first time period (0-T1) whose magnitude is greater than the first threshold value, and is also greater than the predefined noise threshold. In this case, since extremum 30 is attained at time T0a, which is within the first time period (0-T1), processor 28 identifies extremum 30 as the candidate activation point for the first time period.

(iv) Processor 28 identifies the global extremum 32 of the signal within T3 from T0a, i.e., between T0a and T0a+T3. Global extremum 32 is attained at time T0c.

(v) Processor 28 calculates a second threshold value by multiplying the magnitude of extremum 32 by coefficient C.

(vi) Processor 28 calculates a threshold for the second time period (T1-2T1) by taking the minimum of the first threshold value and the second threshold value. Processor 28 then selects the highest-magnitude point 34, attained at time T0b in the second time period, as a candidate activation point, given that the magnitude of point 34 is greater than the both the threshold for the second time period and the predefined noise threshold.

Processor 28 then repeats steps (iv)-(vi) for the third time period (2T1-3T1). That is, processor 28 identifies the global extremum of the signal within T3 from T0b (i.e., between T0b and T0b+T3), calculates a third threshold value by multiplying the magnitude of this extremum by C, sets the threshold for the third time period to the minimum of the second threshold value and the third threshold value, and then selects the highest-magnitude point in the third time period whose magnitude is greater than both the threshold for the third time period and the predefined noise threshold. This point is extremum 32.

Processor 28 then repeats steps (iv)-(vi) for the fourth time period, and thus selects another candidate activation point 38, which is attained at time T0d. The remainder of the time periods are similarly processed.

As described above, following the selection of the set of candidate activation points, processor 28 prunes the set, by removing one of any pair of candidates that are within an interval T2 of one another. For example, for any pair of the candidate activation points that are within T2 of one another and are respectively not within T2 of any other one of the candidates, processor 28 may remove the one of the pair having the smaller magnitude than that of the other one of the pair. If a particular candidate is within T2 of both a preceding candidate and a subsequent candidate, processor 28 may remove the particular candidate, even if the magnitude of the particular candidate is greater than the respective magnitudes of the two neighboring candidates. Thus, for example, in the case shown in FIG. 2, extremum 32 may be removed from the set of candidates if T0c is within T2 of both T0b and T0d. The candidate points that remain following the pruning are indicated in FIG. 2 by respective star-shaped markers. These star-shaped markers, and/or any other suitable markers (e.g., circles or arrows), may be provided on a graphical display to the EP physician as "annotations" to the intracardiac signal obtained via the EP catheter, as described above with reference to FIG. 1.

Typically, T1 is slightly greater than the minimum expected cycle length; for example, T1 may be between 80 and 120 ms. If T1 were less than this, processor 28 might select a relatively large number of false candidate activation points, i.e., candidate points that do not actually correspond to activations. Conversely, if T1 were greater than this, processor 28 might miss some activations.

Typically, T2 is approximately equal to the minimum expected cycle length; for example, T2 may also be between 80 and 120 ms. Such a value of T2 facilitates removing false candidate activation points without a significant risk of removing true activation points.

Typically, T3 is approximately equal to the maximum expected cycle length; for example, T3 may be between 250 and 350 ms. Such a value of T3 facilitates calculating, for each time period, a threshold that reflects the behavior of the signal near the time period.

In general, a suitable value for the coefficient C may be obtained by experimentation. The present inventors have found that a value between 0.1 and 0.5 is generally effective, at least for bipolar signals.

Following the pruning of the set, processor 28 generates an output that is based on the points remaining in the set corresponding to respective activations of the tissue. For example, as described above with reference to FIG. 1 and further shown in FIG. 2 by virtue of the star-shaped markers, processor 28 may annotate the signal to indicate that the points remaining in the set correspond to respective activations of the tissue.

Alternatively or additionally, by calculating at least one time interval between two of the points remaining in the set, processor 28 may calculate a cycle length from the points remaining in the set. For example, processor 28 may calculate the time interval between two consecutive points, or the mean or median of multiple such intervals. (For example, in the case shown in FIG. 2, processor 28 may calculate a cycle length of T0b–T0a or (T0c–T0a)/2.) Processor 28 may then display the calculated cycle length on display 26.

In some embodiments, processor 28 performs the above-described activation-point-selection technique for each of a plurality of signals sensed by different respective electrodes located at different respective areas of the tissue. In such embodiments, processor 28 may calculate the cycle length for each of the areas of tissue as described above, and then show these cycle lengths on an electroanatomical map of the areas. For example, processor 28 may color areas having different respective cycle lengths in different respective colors, in accordance with a predefined color scale.

Alternatively or additionally, processor 28 may identify the activation sequence of the different areas, based on the order across the signals in which the activations occur. For example, processor 28 may receive (i) a first signal, shown in FIG. 2, sensed by a first electrode in contact with a first area of tissue, and (ii) a second signal, sensed by a second electrode in contact with a second area of tissue. If, by processing the second signal as described above, processor 28 identifies activations that occur, respectively, slightly after (e.g., less than 80 ms after) T0a, T0b, and T0d, processor 28 may ascertain that the second area is activated after the first area during each cycle. Conversely, if processor 28 identifies activations that occur, respectively, slightly before T0a, T0b, and T0d, processor 28 may ascertain that the second area is activated before the first area during each cycle.

Alternatively or additionally to identifying the activation sequence, processor 28 may calculate the propagation time required for the activation wavefront to propagate through the multiple areas of tissue, by calculating the interval between the first and last activations that were identified for a particular cardiac cycle, or the mean or median of this interval over multiple cardiac cycles. For example, given (i) a first activation, in the first area, occurring at T0a, (ii) a second activation, in the second area, occurring 15 ms after T0a, and (iii) a third activation, in a third area, occurring 30 ms after T0a, processor 28 may calculate a propagation time of 30 ms. Processor 28 may further compare the cycle length of one or more of the signals to the propagation time. If the fraction of the propagation time to the cycle length is greater than a predefined threshold, processor 28 may generate an output indicating a possible rotational activation.

Figure 3:
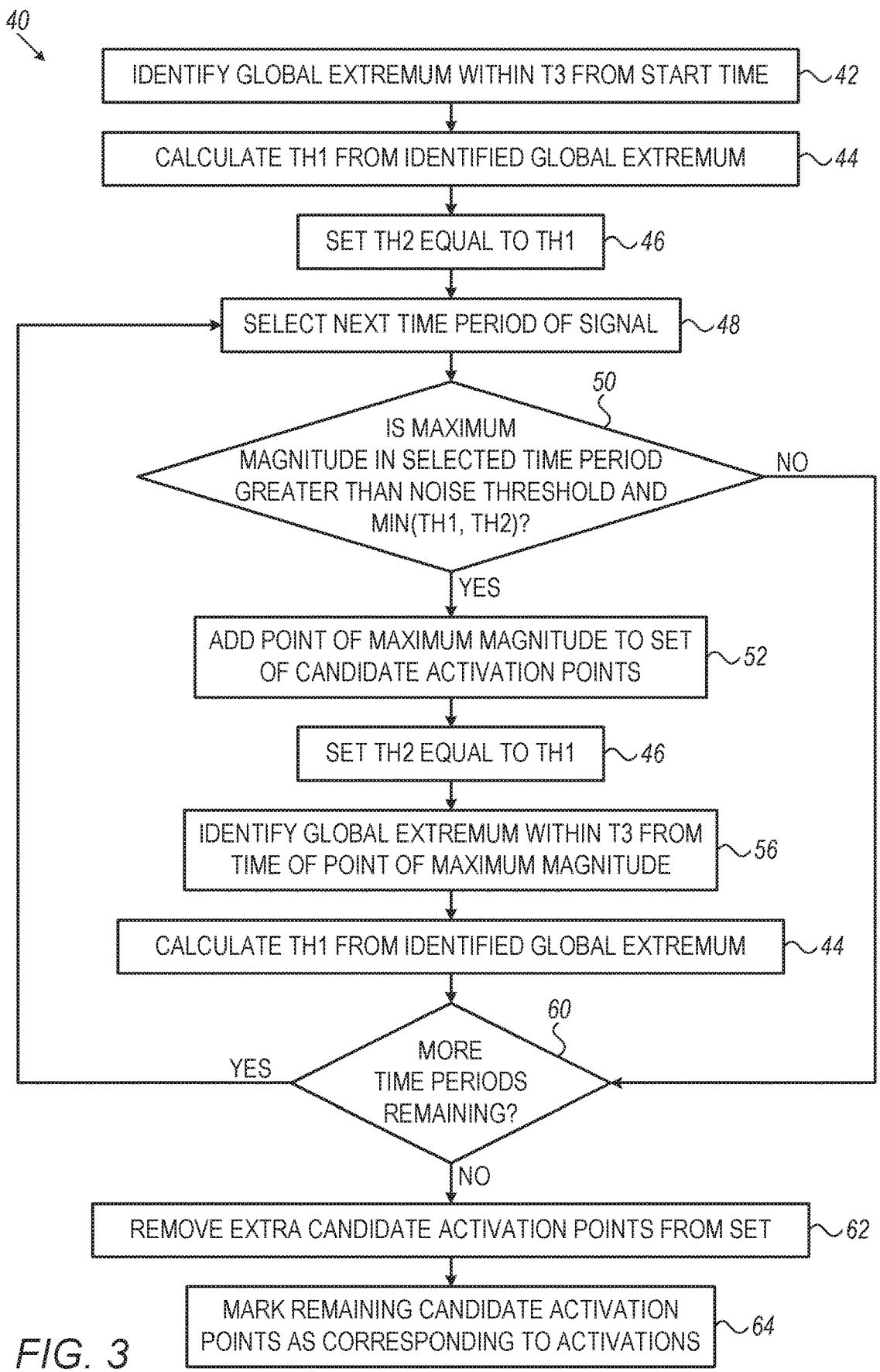
FIG. 3 is a flow diagram for a method for annotating an electrogram signal, in accordance with some embodiments of the present invention.

Reference is now made to FIG. 3, which is a flow diagram for a method 40 for annotating an electrogram signal, in accordance with some embodiments of the present invention. Method 40 may be performed by processor 28 (FIG. 1) via the execution of any suitable software program.

Method 40 begins with the initialization of two variables: a first threshold variable TH1, and a second threshold variable TH2. To perform this initialization, processor 28 first identifies the global extremum of the signal within T3 from the start time of the signal, at a first global-extremum-identifying step 42. Next, processor 28, at a TH1-calculating step 44, calculates TH1 from the identified global extremum. For example, as described above with reference to FIG. 2, processor 28 may calculate TH1 by multiplying the identified global extremum by a predefined coefficient. Next, at a TH2-setting step 46, processor 28 sets TH2 equal to TH1.

Subsequently, processor 28 builds a set of candidate activation points, by iteratively processing the time periods spanned by the signal. At the start of each iteration, at a time-period-selecting step 48, processor 28 selects the next time period of the signal. Processor 28 then checks, at a first checking step 50, whether the maximum magnitude (i.e., absolute value) of the signal in the selected time period is greater than both a predefined noise threshold and the minimum of TH1 and TH2. If yes, processor 28, at a point-adding step 52, adds the point of maximum magnitude to the set of candidate activation points. Processor 28 then sets second threshold TH2 equal to first threshold TH1, at TH2-setting step 46. Subsequently, at a second global-extremum-identifying step 56, processor 28 identifies the global extremum of the signal within T3 from the time of the point of maximum magnitude. Processor 28 then updates TH1 at TH1-calculating step 44, using the newly-identified global extremum.

Subsequently to updating TH1, or if processor 28 does not identify a suitable candidate activation point at first checking step 50, processor 28 checks, at a second checking step 60, whether any time periods remain. If yes, processor 28 returns to time-period-selecting step 48, and then processes the next time period of the signal.

Following the processing of the last time period, processor 28, at a removing step 62, removes the extra candidate activation points from the set, as described above with reference to FIG. 2. Finally, at a marking step 64, processor marks the remaining candidate activation points as corresponding to respective activations. As described above with reference to FIG. 2, processor 28 may alternatively or additionally generate any other type of output that assumes that each of the remaining candidate activation points corresponds to a respective activation.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. For example, where methods and steps are described above as being performed in a certain order, it is intended that the methods and steps do not have to be performed in the order described; rather, any order that allows the embodiments to function for their intended purposes is included in the scope of the present invention.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
an electrical interface; and
a processor, configured to:
receive, via the electrical interface, a signal sensed by at least one electrode in contact with tissue of a heart of a subject, the signal spanning successive time periods that are each of length T1 and including multiple signal points, wherein the time periods include a first time period, a second time period that immediately follows the first time period, and a third time period that immediately follows the second time period
calculate respective thresholds for the time periods,
select a set of points that includes, for each of the time periods, a signal point of greatest magnitude in the time period, provided that the greatest magnitude is greater than the threshold for the time period, wherein the set of points includes a first-period signal point in the first time period and a second-period signal point in the second time period
remove, from the set, one of any pair of the selected points that are within an interval T2 of one another, the interval T2 being less than T1, the interval T2 comprises a first interval and
generate an output that is based on the points remaining in the set corresponding to respective electrical activations of the tissue,
identify a first global extremum of the signal within a second interval T3 from the first-period signal point, and
identify a second global extremum of the signal within the second interval T3 from the second-period signal point, and
wherein the processor is configured to calculate the threshold for the third time period as a product of (a) a coefficient that is less than one, and (b) a minimum of (i) a first-global-extremum magnitude of the first global extremum and (ii) a second-global-extremum magnitude of the second global extremum.

2. The system according to claim 1, wherein the processor is configured to receive the signal while the heart of the subject experiences atrial fibrillation.

3. The system according to claim 1, wherein T1 comprises a value between approximately 80 and approximately 120 ms.

4. The system according to claim 1, wherein T2 comprises a value between approximately 80 and approximately 120 ms.

5. The system according to claim 1, wherein the coefficient comprises a value from approximately 0.1 to approximately 0.5.

6. The system according to claim 1, wherein T3 comprises a value from about 250 to about 350 ms.

7. The system according to claim 1, wherein the processor is configured to remove, from any pair of the selected points that are within T2 of one another and are respectively not within T2 of any other one of the selected points, one of the pair having a smaller magnitude than that of the other one of the pair.

8. The system according to claim 1, wherein the processor is configured to generate the output by annotating the signal to indicate that the points remaining in the set correspond to the respective electrical activations.

9. The system according to claim 1, wherein the processor is configured to generate the output by:
calculating a length of a cycle of electrical activation from the points remaining in the set, by calculating at least one time interval between two of the points remaining in the set, and
displaying the length of the cycle.

10. A method, comprising:
receiving a signal provided by at least one electrode in contact with tissue of a heart of a subject, the signal spanning successive time periods that are each of length T1 and including multiple signal points, wherein the time periods include a first time period, a second time period that immediately follows the first time period, and a third time period that immediately follows the second time period;
calculating respective thresholds for the time periods;
selecting a set of points that includes, for each of the time periods, a signal point of greatest magnitude in the time period, provided that the greatest magnitude is greater than the threshold for the time period, wherein the selecting the set of points comprises
selecting a first-period signal point in the first time period and a second-period signal point in the second time period;
removing, from the set, one of any pair of the selected points that are within an interval T2 of one another, interval T2 being less than T1, the interval T2 comprises a first interval; and
generating an output that is based on the points remaining in the set corresponding to respective electrical activations of the tissue,
identifying a first global extremum of the signal within a second interval T3 from the first-period signal point;
identifying a second global extremum of the signal within the second interval from the second-period signal point, and
calculating the threshold for the third time period as a product of (a) a coefficient that is less than one, and (b) a minimum of (i) a first-global-extremum magnitude of the first global extremum and (ii) a second-global-extremum magnitude of the second global extremum.

11. The method according to claim 10, wherein receiving the signal comprises receiving the signal while the heart of the subject experiences atrial fibrillation.

12. The method according to claim 10, wherein T1 is comprises a value between 80 and 120 ms.

13. The method according to claim 10, wherein T2 comprises a value between 80 and 120 ms.

14. The method according to claim 10, wherein the coefficient comprises a value between approximately 0.1 and approximately 0.5.

15. The method according to claim 10, wherein T3 comprises a value from about 250 to about 350 ms.

16. The method according to claim 10, wherein the removing comprises removing, from any pair of the points that are within T2 of one another and are respectively not within T2 of any other one of the points, one of the pair having a smaller magnitude than that of the other one of the pair.

17. The method according to claim 10, wherein generating the output comprises annotating the signal to indicate that the points remaining in the set correspond to the respective electrical activations.

18. The method according to claim 10, wherein generating the output comprises:
   calculating a length of a cycle of electrical activation from the points remaining in the set, by calculating at least one time interval between two of the points remaining in the set; and
   displaying the length of the cycle.

\* \* \* \* \*